United States Patent [19]

Wochok et al.

[11] Patent Number: 4,478,000
[45] Date of Patent: Oct. 23, 1984

[54] PROCESS FOR STIMULATING ASEXUAL PROPAGATION OF *SIMMONDSIA CHINENSIS* TISSUE

[75] Inventors: Zachary S. Wochok, Manchester, Mo.; Carolyn J. Sluis, Davis, Calif.

[73] Assignee: Plant Resources Institute, Salt Lake City, Utah

[21] Appl. No.: 446,378

[22] Filed: Dec. 2, 1982

Related U.S. Application Data

[63] Continuation-in-part of Ser. No. 230,014, Jan. 30, 1981, abandoned.

[51] Int. Cl.³ ............................................. A01G 1/00
[52] U.S. Cl. ........................................................ 47/58
[58] Field of Search ............................................ 47/58

[56] References Cited

PUBLICATIONS

Article–JoJoba Reports, "Micropropagation for Jojoba Improvement Programs," by Zachary S. Wochok & Carolyn J. Sluis, No. 26, Mar. 1979, pp. 1–5.
Birnbaum, Elliott, Dept. of Natural Products, Institute for Applied Research, Ben–Gurion University of the Negev, Beer–Sheva, Israel, 1978, *Simmondsia chinensis:* Studies by Tissue Culture, pp. 243–252 in A. W. Alfermann and E. Reinhard, eds., Production of Natural Compounds by Cell Culture Methods.
Mandani, A., C. W. Lee and L. Hogan, 1978, *In vitro* propagation of *Simmondsia chinensis* Via Shoot Tip Cultures, HortScience 13(3):35.
Rost, T. L. et al., The Production of Jojoba Wax in Tissue Culture, p. 14 in Abstracts, Third International Conference on Jojoba, Riverside, California, Sep. 13–16, 1978, 18 p.
Hogan, LeMoyne, Chi Won Lee, David A. Palzkill and William R. Feldman, "Recent Progress in the Propagation of Jojoba by Stem Cuttings", pp. 1–4 in a Report of a Third International Conference on Jojoba, Riverside, California, Sep. 13–16, 1978.
Tautvydas, Kestutis J. "Organogensis in Tissue Culture of Jojoba (*Simmondsia chinensis*)," pp. 25–38 in a Report of a Third International Conference on Jojoba, 1978.
Rost. T. L. and Maud A. W. Hinchee, Preliminary Report of the Production of Callus, Organogensis and Regeneration of Jojoba (*Simmondsia Chinensis*, Link, Schneid. ) in Tissue Culture, pp. 299–305 in Journal of Horticultural Science (1980) 55 (3).

*Primary Examiner*—Robert E. Bagwill

[57] ABSTRACT

The present invention embodies a process for mass propagation of plant tissue preferably of a *Simmondsia chinensis*, commonly known as Jojoba, and plant tissue having similar characteristics thereto. The process is directed to asexual reproduction of plantlets from tissue of immature and mature plants from a single piece of donor tissue and involves performing the steps thereon of: sterilization; chemical pretreatment with a cytokinin to increase the likelihood of tissue survival; washing again in sterile water; placing and retaining for a specified period the prepared tissue on first and second culture media to support and stimulate tissue and shoot development; separating the shoots by surgical division and transferring to a shoot multiplication medium for further development for a desired period; then transferring to a rooting medium for development into plantlets which are then transferred to a soil mix. The process of the present invention including the steps of the chemical pretreatment soak in a cytokinin of preferred concentrations; the use of certain chemicals in the culture media are complementary to the pretreatment soak and provide for an increase in plantlet survival and multiplication over former processes.

16 Claims, 2 Drawing Figures

PROCESS FOR STIMULATING ASEXUAL PROPAGATION OF *SIMMONDSIA CHINENSIS* TISSUE

RELATED APPLICATION

This application is a continuation in part of our co-pending application Ser. No. 230,014 filed Jan. 30, 1981 now abandoned entitled "Process For Stimulating Asexual Propagation of Simmondsia Chinensis Tissue."

BACKGROUND OF THE INVENTION

1. Field

The present invention relates to processes for stimulating asexual reproduction of plantlets from tissue of immature and mature plants, particularly a variety known as *Simmondsia chinensis*, that are commonly referred to as Jojoba plants.

2. Prior Art

Asexual reproduction commonly involves cutting of a plant shoot proximate to a bud, across a limb, or the like, to form apical or lateral explants. Such explants are rooted in a medium that stimulates growth, for eventual transplant of the plantlets into soil. Thereby, an exact reproduction or clone, of the original tissue is produced. Asexual reproduction makes possible a duplication of desired characteristics of the original plant, as either found in nature or as produced from seedlings. Such cloned plant can then be used to produce seeds or for cross-pollination with other plants to further improve the species or the like. With the present process, plants can be uniformly produced that have improved pollen yield, superior growth form, or have a desired frost tolerance, moisture tolerance, salt tolerance, seed clustering or seed oil content. Thereby, desirable plant characteristics can be optimized for either a certain locale or to produce a maximum seed yield. The process of the present invention enables the duplication of *Simmondsia chinensis*, or Jojoba plants selected to have characteristics of superior seed size and or oil content. Such Jojoba oil is very similar to sperm whale oil, and therefore has important commercial potential as a commodity crop.

Processes for stimulating asexual reproduction of plants from tissue, of course, take into account the particular physical characteristics of that plant or plant family and similarly the process of the present invention has been developed for the *Simmondsia chinesis*, or Jojoba. However, it should be understood that this process may be suitable for plants having characteristics similar thereto, which characteristics include woody stem tissue, shrub-like morphology, and the like.

Heretofore, and with some similarities to the present process, certain processes have been developed for stimulating asexual reproduction of plants, to include the steps of: preparation of plant tissue by appropriately cutting a plant shoot at a limb joint to form an apical explant or across a limb to form a lateral explant, stimulating growth of that explant on a culture medium and rooting on a shoot multiplication medium. Heretofore, pretreatment of such explants has, however, generally involved only a washing in a sterile water than can be dionized or distilled, and has not, as does the present invention, involved a washing in a solution containing a cytokinin. This pretreatment step of the present invention is then chemically complemented by an inclusion of certain hormones to the culture medium that balance with the chemicals used in the pretreatment step so as to provide improved plant growth and increased plant survival rates, and to allow explants to continue to develop thereon for extended time periods without developing callus tissue.

While both the use of conditioning and shoot multiplication mediums are essentially known in the art for stimulating asexual plant reproduction, none have heretofore included both the pretreatment soak in a cytokinin and complementary hormonal chemical additions to the culture medium of the present invention. A pretreatment soak is, however, shown in a U.S. Pat. by Abo, No. 4,217,730, but expressly excludes using a cytokinin in that soak and so is unlike the present process. Examples of other former processes are shown in U.S. Pat. by Corlett, Jr., et al., No. 3,683,550; by Gudin, et al., U.S. Pat. No. 3,816,960; and Sibi, et al., U.S. Pat. No. 4,003,156; and in a patent by McCormick issued in Great Britain and assigned No. 1,387,821.

SUMMARY OF THE INVENTION

It is, therefore, a general object of the present invention to provide a process for efficiently and economically reproducing a large number of plantlets from immature and mature *Simmondsia chinensis* (Jojoba) plant tissue.

It is an additional object of the present invention to provide a process that includes a pretreatment wash step with a chemical from a family of cytokinins, whereby improved explant multiplication and explant survival is obtained.

An additional object of the process of the present invention is to provide, with a step in the process, a culture medium that is chemically complementary to the chemical used in the pretreatment step whose use provides for a lengthening of the time period during which a productive development of explants on that culture medium can be obtained.

An additional object of the practice of the process of the present invention is to provide a plant tissue culture process that is suitable for mass producing a large number of plantlets from a single donnor plant tissue.

In accordance with the above objects, the process of the present invention for asexual propagation of *Simmondsia chinensis* (Jojoba) plant tissue can be broadly defined as including three stages: (a) cytokinin pretreatment; (b) tissue and shoot development; and (c) plantlet differentiation through shoot multiplication and root induction of shoots produced in (b). In the first stage, with lateral or apical explant tissue, the process includes the steps of: first sterilizing the plant tissue, then bathing the plant tissue in a cytokinin, followed by one or more optional washes in sterile water and an excising therefrom of exposed tissue ends. The (b) stage includes placing the explant tissue on a first culture media, preferably a modified Murashige and Skoog basal salt media and exposing that tissue to appropriate light spectra so as to produce plant growth. Further tissue and shoot development is then achieved on a second culture media that is preferably the modified Murashige and Skoog basal salt media with certain growth-stimulating additives complementary to the pretreatment cytokinin added thereto. Whereafter, the shoots are separated by surgical methods and transferred to a shoot multiplication medium, stage (c). The shoot multiplication medium is preferably the modified Murashige and Skoog basal salt media with one of a variety of mixtures of $N_6$-benzyladenine and naphthalene acetic acid that provides a media appropriate to shoot multiplication, growth and development. The shoots are then removed from the multiplication medium and placed on an appropriate rooting medium. Whereafter the rooted plantlets are separated and transplanted into appropriate soil, and, preferably, a fixing solution of emollient waxes is sprayed on the plantlets to limit moisture loss therefrom. A product known as Wilt-Pruf® is a preferred fixing solution and is sprayed on the developed leaves, limiting plant dehydration proximate to transplanting.

BRIEF DESCRIPTION OF THE DRAWINGS

In the drawings that illustrate that which is presently regarded as the best mode for carrying out the invention.

DETAILED DESCRIPTION

Figure 2:
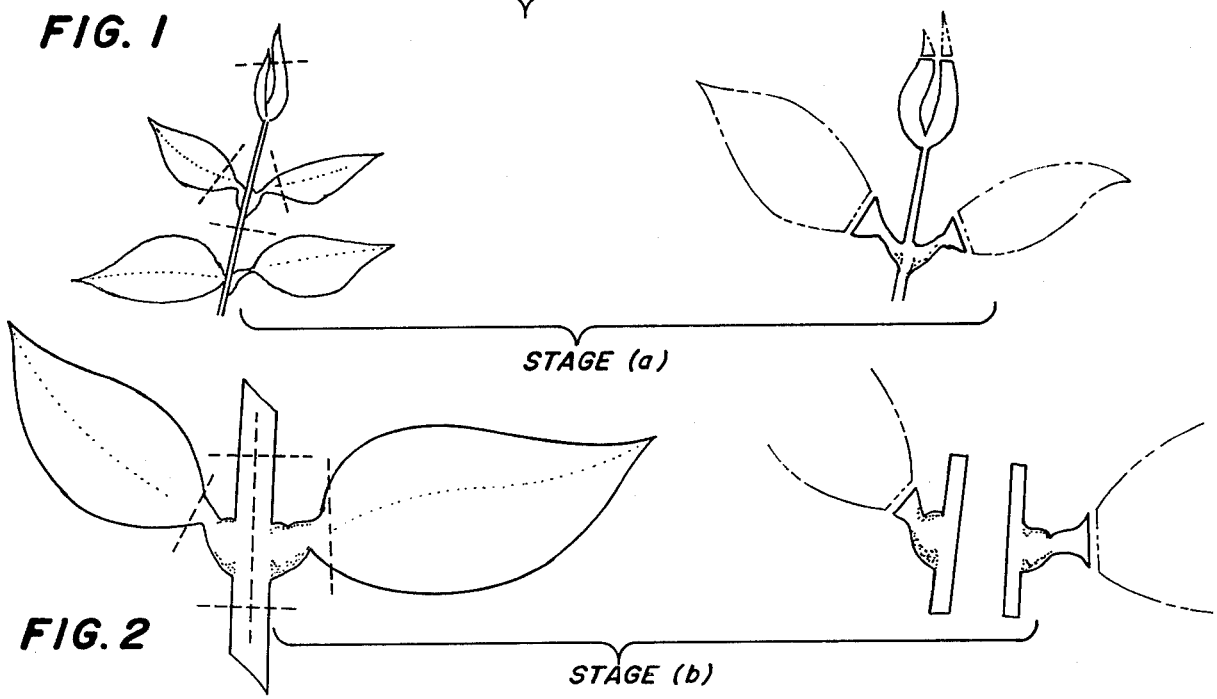
FIG. 2(a) is a schematic showing, with broken lines, how a plant shoot or branch is cut at a bud to form an apical explant, the removed cut portions shown in broken lines.
FIG. 2(b) is a schematic showing, with broken lines, how a plant shoot or branch is cut thereacross to form a lateral explant, the removed cut portions shown in broken lines.

The present invention relates to processes for asexual reproduction of plant tissue wherefrom plantlets are grown that exactly duplicate desired characteristics of the donor plant. The preferred process involves surgical cutting a living plant stem, branch, or the like, that contains axillary buds of immature or mature plants. The present process was developed for *Simmondsia chinensis*, or Jojoba plant, but may also be appropriate to plants having characteristics similar thereto to include woody stem tissues, shrub-like morphology, and the like. Donor tissue is produced, as shown in FIGS. 2(a) and 2(b), as either apical or lateral tissue, apical meaning tissue that is produced by cutting at a bud while lateral involves cutting along a branch, separating a bud, which tissues are hereafter referred to as explants.

Figure 1:
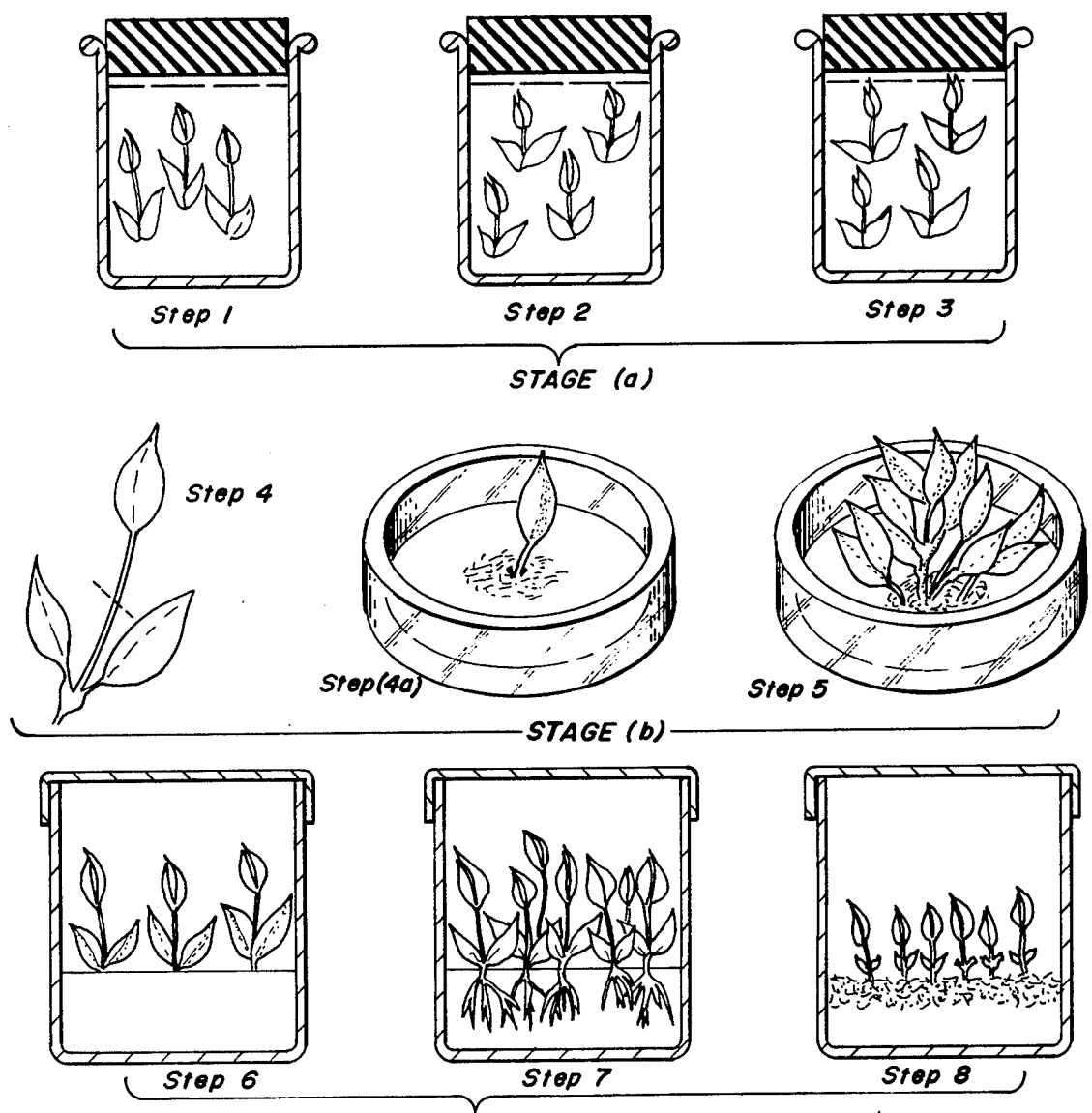
FIG. 1 is a series of schematic representations labeled horizontally as Stages (a), (b) and (c) and numbered as Steps 1 through 8 for illustrating a practicing of the process of the present invention.

Shown in the schematic of FIG. 1, horizontal rows therein are represented as Stages (a), (b), and (c) which identify groups of steps 1 through 8 in practicing the present process as: (a) cytokinin pretreatment; (b) tissue and shoot development; and (c) plantlet differentiation through shoot multiplication and root induction of shoots produced in (b).

Step 1 of Stage (a) should be understood to represent plant tissue being washed within beaker, to provide a sterilization of that tissue. A preferred solution found to be satisfactory in practice could be either a 0.7875% sodium hypochlorite or 15% hydrogen peroxide. Each of which solutions should include one drop of TWEEN-20 per liter, and the explants should remain therein for approximately ten minutes. Preferably, this sterilization is performed under vacuum, as illustrated by the closed vessel of FIG. 1, and constant agitation should be provided thereto to minimize the likelihood of contamination. Obviously, other appropriate sterilization solutions could be substituted for that above-described, and the period of agitation could be shortened or lengthened appropriately so long as the explants are fully sterilized. Such sterilization step and the solutions for use therewith are common within the practices of the industry.

In Step 2 of Stage (a), the explants are also shown within a beaker that represents soaking the sterile explants for approximately ten minutes in a sterile deionized water solution that contains a cytokinin that is a synthetic plant hormone, at approximately a pH of $7.0 \pm 0.5$.

Table 1 hereinbelow that is identified as "Pretreatment Grid" shows a single grid run over a three-week period on nine hundred (900) explants taken from seedlings in moderately poor condition. The first vertical column thereof shows different concentrations (in mg/liter or parts per million) of certain cytokinins used in the pretreatment Step 2. Therein the cytokinins are shown as: BA for $N_6$-benzyladenine, 6DMAP for 6-gammma-gamma-dimethyallyl amino purine; and K for kinetin. The second and third vertical columns identified as Apical Explants and Lateral Explants respectively show: a first number that indicates the number of surviving explants after the three-week period; followed by a slash and a second number that indicates the sample size. Table 1 is divided into horizontal groupings of explants treated with different concentrations of certain cytokinins. The first horizontal grouping of explants is shown as having been treated with BA, or $N_6$-benzyladenine. Therein, acceptable apical explant survival rates are shown as having been obtained at concentrations of two, three and four hundred parts per million, of, respectively, twelve, fifteen and twenty-six explants surviving from a sample of thirty explants. In the same horizontal groupings, lateral explants, pretreated with the same concentrations of two, three and four hundred parts per million, showed a survival rate of, two, four and twelve explants per thirty explants, respectively.

A middle horizontal grouping in Table 1 shows results produced with another cytokinin 6DMAP, or 6-gamma-gamma-dimethylallyl amino purine. Therein, also, solutions containing from one hundred to five hundred parts per million were tested on thirty samples each of apical and lateral explants. Again, as shown therein, concentrations ranging from two to four hundred parts per million of 6 DMAP produced the best apical explant survival and except for concentrations of two hundred parts per million of the cytokinin, a poor but fairly similar survival rate was obtained for all the tested concentrations on the lateral explants.

Therefore, from this experimental data, it is shown that best results for both apical and lateral explants came with concentrations of four hundred and three hundred parts per million for BA and 6DMAP, respectively. Considering the moderately poor condition of the seedlings, generally concentrations between two and four hundred parts per million of both BA and 6DMAP produced acceptable results for both types of explants.

Both types of explants which were treated with BA and 6DMAP appeared to be healthy and look to have a good probability for survival. Considering, as shown in the Note for Table 1, that all explants of the sample were taken from seedlings that were rated to be in moderately poor condition at the greenhouse, the survival rate, particularly at four hundred parts per million for BA, was excellent for both apical and lateral explants.

TABLE I

PRETREATMENT GRID

| | Apical Explants | Lateral Explants |
|---|---|---|
| 100 mg/l BA | 8/30 | 0/30 |
| 200 mg/l BA | 12/30 | 2/30 |
| 300 mg/l BA | 15/30 | 4/30 |
| 400 mg/l BA | 26/30 | 12/30 |
| 500 mg/l BA | 5/30 | 0/30 |
| 100 mg/l 6DMAP | 9/30 | 2/30 |
| 200 mg/l 6DMAP | 15/30 | 1/30 |
| 300 mg/l 6DMAP | 20/30 | 6/30 |
| 400 mg/l 6DMAP | 14/30 | 4/30 |
| 500 mg/l 6DMAP | 12/30 | 2/30 |
| 100 mg/l K | 0/30 | 0/30 |
| 200 mg/l K | 0/30 | 0/30 |
| 300 mg/l K | 0/30 | 0/30 |
| 400 mg/l K | 6/30 | 0/30 |
| 500 mg/l K | 4/30 | 1/30 |

NOTES:
Grid run for 3 weeks; contamination not critical; cultures kept in culture room for duration of grid; K grown explants look different from rest (stunted); all explants taken from seedlings which were in moderately poor condition at the greenhouse; total number of explants = 900 (60 per pretreatment).

Table 1 further shows, across a bottom grouping thereof, a treatment of samples of thirty explants each with one hundred to five hundred parts per million of a cytokinin identified as "K", for kinetin. From Table 1, it is shown that survival rates for explants so treated were very poor. Further, explants pretreated with K were described as looking different from those treated with BA and 6DMAP in that they were stunted and even the explants calssified as survivors did not appear to be healthy.

Step 3 of Stage (a), FIG. 1, shows the explants, after treatment with a cytokinin, being further washed in a vessel containing a deionized or distilled sterile water solution. This washing is not absolutely essential to the invention, but is preferable. Whereafter, as shown in FIG. 1, in the middle horizontal grouping of steps, identified as Stage (b), exposed explant tissue ends are excised, as illustrated by a broken line, shown in Step 4, and the remaining portion of the explant is placed on a first culture medium identified as Step 4(a).

The Step 4(a) culture medium is preferably a basal salts medium. Hereinbelow is included a Table 2 that shows the constituents of a preferred basal salts medium that is a modification of a medium commonly identified as Murashige and Skoog, and is hereinafter referred to as "MS". MS is the preferred culture medium of Step 4(a). Table 2 shows, in the right hand column therein, preferred concentrations of the MS salts in milligrams per liter. Preferably, the cultures of explants are kept at the temperature of 26° C., plus or minus 1 degree, and are subject to alternating 16 hours of light with 8 hours of darkness, utilizing light intensity of approximately 100 muE. n-2. During this step, it has been found that the temperature is more critical to explant multiplication rate than is the above-cited ratio of light to darkness or light intensity.

TABLE 2

| Salt | mg/l |
|---|---|
| $NH_4NO_3$ | 1650 |
| $KNO_3$ | 1900 |
| $CaCl_2.2H_2O$ | 440 |
| $MgSO_4.7H_2O$ | 370 |
| $KH_2PO_4$ | 170 |
| $Na_2$-EDTA | 37.3 |
| $FeSO_4.7H_2O$ | 27.8 |
| $H_3BO_3$ | 6.2 |
| $MnSO_4.H_2O$ | 16.9 |
| $ZnSO_4.7H_2O$ | 8.6 |
| KI | 0.83 |
| $Na_2MoO_4.2H_2O$ | 0.25 |
| $CuSO_4.5H_2O$ | 0.025 |
| $CoCl_2.6H_2O$ | 0.025 |

It has been found in practice that it is desirable to complement the MS with hormones compatible with the cytokinin used in the pretreatment step. Thereby, the explants are further growth stimulated, as described, so as to produce desired active growth and opening of axillary buds over periods of time longer than have formerly been possible using an MS culture medium without additives. Absent such chemical complementing, the explants have been found to thrive only for approximately a one-week period. Thereafter, it has been found in practice, that the plant tissue will begin deteriorating and therefore must be removed and the callus excised prior to introduction to a growth medium. Step 5, Stage (b) illustrates the use of a second culture medium containing an additive compound that, combined with MS, complements the cytokinin used in the pretreatment step to provide for desired plant tissue development. The preferred added chemicals and preferred concentrations thereof are shown in Table 3 and are identified hereinafter as "A". Therefore, a preferred second culture medium for practicing Step 5 of the process of the present invention is represented as "MS-A".

TABLE 3

| Component | Concentration (mg/l) |
|---|---|
| myo-inositol | 100 |
| Thiamine hydrochloride | 0.4 |
| sucrose | 30,000 |
| $N_6$-Benzyladenine(BA) | 1 |
| Naphthalene Acetic Acid(NAA) | 0.001 |
| phytagar | 7007 |

The MS-A medium contains, as plant growth regulators, $N_6$-benzyladenine (BA) and naphthalene acetic acid (NAA) in concentrations appropriate to bringing about desired growth and development effects. Such plant growth regulators and their uses are common to asexual reproduction processes and so will not be described in detail herein. Further, the A addition to the MS, it should be understood, is a complement thereto in that, just as the selected pretreatment cytokinin is a hormone used to initiate plant growth cycle, the A components are selected to complement the growth processes initiated by the pretreatment step.

In practice therefore, the preferred chemical components shown in Table 3, identified as A, include growth stimulating hormones that act to provide a continuing stimulation to the explants to encourage active growth and the opening of axillary buds. The explants on the MS-A medium have been found to thrive over residence periods long exceeding that formerly possible and so are usually left thereon for approximately a six-week period. While the components of the A portion of the MS-A medium are preferred, it should be understood that other hormones, or deletions of component chemicals shown in the tables, could be made within the scope of this disclosure. Further, the concentrations shown in table 3 could be varied appropriately to within plus or minus 25 percentages, without departing from the scope of this disclosure, providing a desired hormonal balance is maintained that is compatible with the cytokinin pretreatment.

Shown in the bottom horizontal grouping of steps, identified as Stage (c), is a schematic identified as Step 6. Step 6 represents placement of explant shoots, both lateral and apical, from the MS-A culture medium, after surgical separation thereof, on to a shoot multiplication medium. This separation is like the explant separation that occurs prior to introduction to the culture medium, illustrated as Step 4. The shoot multiplication medium is the basic MS shown in Table 2, that further includes $N_6$-benzyladenine (BA), and naphthalene acetic acid (NAA) in the concentrations set out in Table 4 below.

TABLE 4

| BA/NAA (mg/l) | 0 weeks | 6 weeks | 12 weeks | 18 weeks | 24 weeks |
|---|---|---|---|---|---|
| 0.5/0.0 | No differences | | 28 | 269 | 999 |
| 0.5/0.01 | were observed | | 10 | 14 | 21 |
| 0.5/0.1 | for 0–6 weeks | | 11 | 12 | 14 |
| 0.5/1.0 | at all | | 9 | 11 | 9 |
| 1.0/0.0 | concentrations | | 11 | 53 | 97 |
| 1.0/0.01 | | | 19 | 26 | 62 |
| 1.0/0.1 | | | 9 | 45 | 87 |
| 1.0/1.0 | | | 12 | 106 | 208 |

NOTE: New Jojoba shoots developing from four original explants on six different combinations of BA plus NAA and two concentrations of BA alone during four six-week subculture periods.

Table 4, above, shows development from four original Jojoba shoots, treated as described, to produce explants that were then placed on eight combinations of different concentrations, in milligrams per liter (mg/l), of BA/NAA, as shown in the left hand column. The vertical columns across Table 4, in turn, reflect time in weeks the explants developed at the particular BA/NAA concentrations and the multiplication thereof to that week for a total of a twenty-four week period.

TABLE 5

| BA/NAA (mg/l) | Multiplication Factor (24 weeks) |
|---|---|
| 0.5/0.0 | 249.75 |
| 0.5/0.01 | 5.25 |
| 0.5/0.1 | 3.50 |
| 0.5/1.0 | 2.25 |
| 1.0/0.0 | 24.25 |
| 1.0/0.01 | 15.25 |
| 1.0/0.1 | 21.75 |
| 1.0/1.0 | 52.00 |

NOTE: Normalized shoot multiplication factors for Jojoba explants grown on six different combinations of BA plus NAA and two concentrations of BA alone, at twenty-four weeks consisting of four successive six-week culture periods.

Table 5, above, shows normalized growth development of new Jojoba shoots at twenty-four (24) weeks and illustates a clear preference for certain concentrations of BA and BA plus NAA appropriate for shoot multiplication. As shown in Table 4, shoot multiplication for the Jojoba explants was best for a concentration of 0.5 milligrams per liter of BA above which resulted in new Jojoba shoot developments over the 24-week period of 999 and a normalized multiplication factor of 249.75, shown in Table 5. The second best shoot multiplication occurred at 1.0/1.0 milligrams per liter of BA and NAA which resulted in 208 developed shoots for that 24-week period, and provided a multiplication factor of 52.00, as shown in Table 5. In general, test results on Jojoba tissues, shown in Tables 4 and 5, illustrate that BA alone or in combinations with NAA at a ratio of 1.0/1.0 will produce the best shoot multiplication results, with concentrations therebetween also producing desirable growth.

In practicing the present process, as previously described, desired tissue growth stimulation is obtained on the MS and MS-A mediums. The plant tissues are then subdivided and recultured on the shoot medium for subsequent periods of time. This multiplication process can be continued as many times as required in order to produce a desired number of shoots. Thereafter, as illustrated by Step 7, the multiplied shoots are subdivided and placed on the root initiation medium.

TABLE 6

| Component | Concentration (mg/l) |
|---|---|
| $MgSO_4$ | 720 |
| $Ca(NO_3)_2$ | 300 |
| $Na_2SO_4$ | 200 |
| $KNO_3$ | 80 |
| KCl | 65 |
| $Na_2PO_4$ | 16.5 |
| $MnSO_4.4H_2O$ | 7 |
| $ZnSO_4.H_2O$ | 3 |
| $FeSO_4.7H_2O$ | 2.5 |
| $H_3BO_3$ | 1.5 |
| KI | 0.15 |
| myo-inositol | 100 |
| thiamine hydrochloride | 0.4 |
| sucrose | 1000 |
| 6-gamma-gamma-dimethylallyl amino purine(DMAP) | 0.25 |
| indole butyric acid(IBA) | 1.0 |
| phytagar | 800 |

A preferred root initiation medium is shown in Table 6 above. The concentrations of chemicals shown therein have been found to work well in practice, which concentrations, it should be understood can be varied in practice within a range of plus or minus 25 percent to produce acceptable results. Such root initiation medium is common to asexual reproduction. Thereafter, the rooted shoots, now called plantlets, as shown in Step 8, are separated and transferred to a soil mix, and a fixing solution of emollient waxes, such as a product commonly known as Wilt-Pruf ®, or the like, is sprayed on developed leaves to limit plant dehydration.

It should be understood that the present disclosure is made by way of example and that variations in both the chemical makeup and concentration of the different mediums shown in the tables can be varied, as described, within the scope of the present disclosure. Also, while the use of BA and NAA as growth stimulators is not in and of itself new and unique to asexual reproduction processes, the particular preferred concentrations, as shown in Tables 4 and 5 of ranging from .05/0 to 1.0/1.0, have been found in practice to be complementary to the chemical hormone additives of the pretreatment and culture medium steps. Therefore, the described growth medium, in the combination therewith, along with the pretreatment and culture medium steps, is also believed to be unique and distinct. The cytokinins used in the pretreatment step, shown in Table 1, are, of course, of a family of chemicals but, as shown, it was found that a kinetin was not suitable and, therefore, the pretreatment step of the present invention is limited to the described BA and DMAP combinations. Also, where the process of the present invention has been developed and has been found through testing to be effective with *Simmondsia chinensis* plant tissue (Jojoba), it should be understood that it is believed to be effective and appropriate for use with plants having like or similar characteristics thereto, such as plants that are perennial wood shrubs.

Although preferred steps and constituent chemicals have been shown and described herein for practicing the process of the present invention, it should be understood that the present disclosure is made by way of example only and that variations are possible without departing from the subject matter coming within the scope of the following claims, which claims we regard as our invention.

We claim:

1. A process for initiating mass propagation of plant tissue from undifferentiated *Simmondsia chenensis* plant tissue comprising the steps of, sterilization of the donor tissue; pretreatment of said tissue with a solution containing a cytokinin that is $N_6$-benzyladenine; placing and culturing said treated tissue on a first culture medium appropriate to support and promote tissue growth under appropriate conditions of temperature and light; further culturing the tissue on a second culture medium compatible with the pretreatment step to promote additional tissue growth and shoot development; separating the developed tissue into individual shoots; placing and culturing said shoots on a shoot multiplication medium; separating the multiplied shoots into individual shoots for development on a root initiation medium into plantlets; and transplanting the plantlets into a soil mix.

2. A process for initiating mass propagation of plant tissue as recited in claim 1, wherein the plant tissue is sterilized by agitating it in a solution containing sodium hypochlorite and TWEEN-20.

3. A process for initiating mass propagation of plant tissue as recited in claim 1, wherein the plant tissue is sterilized by agitating it in a solution containing hydrogen peroxide and TWEEN-20.

4. A process for initiating mass propagation of plant tissue as recited in claim 1, wherein the pretreatment solution is maintained at a pH of $7.0 \pm 0.5$.

5. A process for initiating mass propagation of plant tissue as recited in claim 1, wherein the $N_6$-benzyladenine concentration is in a range from 200 ppm to 400 ppm in a sterile water solution.

6. A process for initiating mass propagation of plant tissue as recited in claim 1, further including, after pretreating said tissue, the step of at least one washing of the tissue in a sterile water solution.

7. A process for initiating mass propagation of plant tissue as recited in claim 1, wherein the shoot multiplication medium consists of a modified Murashige and Skoog basal salts medium and $N_6$-benzyladenine(BA)/-naphtalene acetic acid(NAA) in relative concentrations, in milligrams per liter, that range from 0.5BA/0.0NAA to 1.0BA/1.0NAA.

8. A process for initiating mass propagation of plant tissue as recited in claim 1, further including the step of applying a fixing solution of emollient waxes to the plantlet at the time of transfer to a soil mix.

9. A process for initiating mass propagation of plant tissue from undifferentiated *Simmondsia chenensis* plant tissue comprising the steps of, sterilization of the donor tissue; pretreatment of said tissue with a solution containing a cytokinin that is 6-gamma-gamma-dimethyalyl amino purine; placing and culturing said treated tissue on a first culture medium appropriate to support and promote tissue growth under appropriate conditions of temperature and light; further culturing the tissue on a second culture medium compatible with the pretreatment step to promote additional tissue growth and shoot development; separating the developed tissue into individual shoots; placing and culturing said shoots on a shoot multiplication medium; separating the multiplied shoots into individual shoots for development on a root initiation medium into plantlets; and transplanting the plantlets into a soil mix.

10. A process for initiating mass propagation of plant tissue as recited in claim 9, wherein the plant tissue is sterilized by agitating it in a solution containing sodium hypochlorite and TWEEN-20.

11. A process for initiating mass propagation of plant tissue as recited in claim 9, wherein the plant tissue is sterilized by agitating it in a solution containing hydrogen peroxide and TWEEN-20.

12. A process for initiating mass propagation of plant tissue as recited in claim 9, wherein the pretreatment solution is maintained at a pH of $7.0 \pm 0.5$.

13. A process for initiating mass propagation of plant tissue as recited in claim 9, wherein the 6-gamma-gamma-dimethyally amino purine concentration is in a range from 200 ppm to 400 ppm in a sterile water solution.

14. A process for initiating mass propagation of plant tissue as recited in claim 9, further including, after pretreating said tissue, the step of at least one washing of the tissue in a sterile water solution.

15. A process for initiating mass propagation of plant tissue as recited in claim 9, wherein the shoot multiplication medium consists of a modified Murashige and Skoog basal salts medium and $N_6$-benzyladenine(BA)/-naphtalene acetic acid(NAA) in relative concentrations, in milligrams per liter, that range from 0.5BA/0.0NAA to 1.0BA/1.0NAA.

16. A process for initiating mass propagation of plant tissue as recited in claim 9, further including the step of applying a fixing solution of emollient waxes to the plantlet at the time of transfer to a soil mix.

* * * * *